(12) United States Patent
Blount et al.

(10) Patent No.: US 8,301,626 B2
(45) Date of Patent: Oct. 30, 2012

(54) METHOD AND APPARATUS FOR MAINTAINING AND PROCESSING PROVENANCE DATA IN DATA STREAM PROCESSING SYSTEM

(75) Inventors: Marion Lee Blount, Mahopac, NY (US); John Sidney Davis, II, Arlington, VA (US); Maria Rene Ebling, White Plains, NY (US); Archan Misra, Bridgewater, NJ (US); Daby Mousse Sow, Croton on Hudson, NY (US); Min Wang, Cortlandt Manor, NY (US)

(73) Assignee: International Business Machines Corporation, Armonk, NY (US)

( * ) Notice: Subject to any disclaimer, the term of this patent is extended or adjusted under 35 U.S.C. 154(b) by 713 days.

(21) Appl. No.: 12/125,212

(22) Filed: May 22, 2008

(65) Prior Publication Data

US 2009/0292729 A1 Nov. 26, 2009

(51) Int. Cl.
G06F 17/30 (2006.01)
G06F 7/00 (2006.01)
(52) U.S. Cl. ......... 707/736; 707/803; 707/769; 707/758
(58) Field of Classification Search .................. 707/736, 707/803, 769, 758
See application file for complete search history.

(56) References Cited

U.S. PATENT DOCUMENTS

| | | | |
|---|---|---|---|
| 6,131,091 A | 10/2000 | Light | |
| 6,594,773 B1 | 7/2003 | Lisitsa et al. | |
| 6,658,477 B1 | 12/2003 | Lisitsa et al. | |
| 6,725,287 B1 | 4/2004 | Loeb et al. | |
| 6,748,440 B1 | 6/2004 | Lisitsa et al. | |
| 6,983,286 B1 | 1/2006 | Sinha et al. | |
| 7,010,538 B1 | 3/2006 | Black | |
| 7,194,000 B2 | 3/2007 | Balachandran et al. | |
| 7,222,182 B2 | 5/2007 | Lisitsa et al. | |

(Continued)

FOREIGN PATENT DOCUMENTS

EP 0852440 A2 7/1998

OTHER PUBLICATIONS

Vijayakumar et al., "Tracking Stream Provenance in Complex Event Processing Systems for Workflow-Driven Computing," VLDB, Sep. 2007.*

(Continued)

*Primary Examiner* — Kuen Lu
(74) *Attorney, Agent, or Firm* — Preston J. Young; Ryan, Mason & Lewis, LLP

(57) ABSTRACT

Techniques are disclosed for maintaining and processing provenance data in such data stream processing systems. For example, a method for processing data associated with a data stream received by a data stream processing system, wherein the system comprises a plurality of processing elements, comprising the following steps. A portion of data associated with the data stream is maintained. The maintained data comprises inputs to each processing element that contributed to an output of each processing element. In response to an alert generated by one of the processing elements, a scheduler is triggered to determine when a pre-calculation of a prospective query related to the alert should be executed. In response to the scheduler, at least a portion of the maintained data is used to determine a set of data that contributed to the alert such that the alert-contributing set of data can be used to respond to the prospective query upon arrival thereof.

16 Claims, 5 Drawing Sheets

U.S. PATENT DOCUMENTS

| | | |
|---|---|---|
| 7,240,065 B2 | 7/2007 | Yang et al. |
| 7,246,157 B2 | 7/2007 | Cianciarulo et al. |
| 7,251,660 B2 | 7/2007 | Yang et al. |
| 7,680,797 B1 * | 3/2010 | Singh et al. .................. 707/781 |
| 2003/0076784 A1 | 4/2003 | Ta et al. |
| 2003/0084179 A1 | 5/2003 | Kime et al. |
| 2003/0126276 A1 | 7/2003 | Kime et al. |
| 2004/0117037 A1 | 6/2004 | Hinshaw et al. |
| 2005/0010510 A1 | 1/2005 | Brose et al. |
| 2005/0185578 A1 | 8/2005 | Padmanabhan et al. |
| 2006/0004802 A1 | 1/2006 | Phillips et al. |
| 2006/0126713 A1 | 6/2006 | Chou et al. |
| 2006/0149849 A1 | 7/2006 | Raz |
| 2006/0197766 A1 | 9/2006 | Raz |
| 2006/0288045 A1 | 12/2006 | Raz |
| 2007/0043565 A1 | 2/2007 | Aggarwal et al. |
| 2009/0024608 A1 * | 1/2009 | Deolalikar ...................... 707/5 |

OTHER PUBLICATIONS

Lempel et al., "Predictive Caching and Prefetching of Query Results in Search Engines," ACM, 2003.*

Moreau et al., "The Provenance of Electronic Data," Communications of the ACM, Apr. 2008.*

C. E. Shannon, "A Mathematical Theory of Communication," Bell System Technical Journal, Jul. and Oct. 1948, pp. 1-55 , vol. 27.

M. Blount et al., "Century: Automated Aspects of Patient Care," 13th IEEE International Conference on Embedded and Real-Time Computing Systems and Applications (RTCSA), 2007, 6 pages.

M. Blount et al., "A Time-and-Value Centric Provenance Model and Architecture for Medical Event Streams," Healthnet, Jun. 2007, pp. 95-100, Puerto Rico.

* cited by examiner

100

200

600

METHOD AND APPARATUS FOR MAINTAINING AND PROCESSING PROVENANCE DATA IN DATA STREAM PROCESSING SYSTEM

CROSS REFERENCE TO RELATED APPLICATION

The present application is related to U.S. patent application identified as application Ser. No. 12/125,219, entitled "Method and Apparatus for Determining and Validating Provenance Data in Data Stream Processing System," and filed concurrently herewith, the disclosure of which is incorporated herein.

FIELD OF THE INVENTION

The present invention relates to data stream processing systems and, more particularly, to techniques for maintaining and processing provenance data in such data stream processing systems.

BACKGROUND OF THE INVENTION

Numerous types of information arrive in the form of a stream. Examples include video and audio as well as data generated by medical sensors such as electroencephalogram (EEG) or electrocardiogram (ECG) data, and the like.

These data streams frequently require processing before they can be stored or reviewed. Many existing systems have been built to process and manage streaming data. Often these systems flow the stream of data through a graph of processing elements, each step in the graph applying a different type of processing logic that yields some form of an analytic result.

However, it has been realized that a need exists to determine precisely what sequence of processing elements participated in the generation of an analysis result and what stream data samples contributed to the generation of the analysis result. These are called respectively the process provenance and the data provenance of the analysis result.

SUMMARY OF THE INVENTION

Principles of the invention provide techniques for maintaining and processing provenance data in such data stream processing systems.

For example, in one embodiment of the invention, a method for processing data associated with a data stream received by a data stream processing system, wherein the system comprises a plurality of processing elements, comprising the following steps. A portion of data associated with the data stream is maintained. The maintained data comprises inputs to each processing element that contributed to an output of each processing element. In response to an alert generated by one of the processing elements, a scheduler is triggered to determine when a pre-calculation of a prospective query related to the alert should be executed. In response to the scheduler, at least a portion of the maintained data is used to determine a set of data that contributed to the alert such that the alert-contributing set of data can be used to respond to the prospective query upon arrival thereof.

Advantageously, such inventive techniques are able to determine precisely what sequence of processing elements participated in the generation of an analysis result and what stream data samples contributed to the generation of the analysis result.

These and other objects, features and advantages of the present invention will become apparent from the following detailed description of illustrative embodiments thereof, which is to be read in connection with the accompanying drawings.

DETAILED DESCRIPTION

Figure 1:
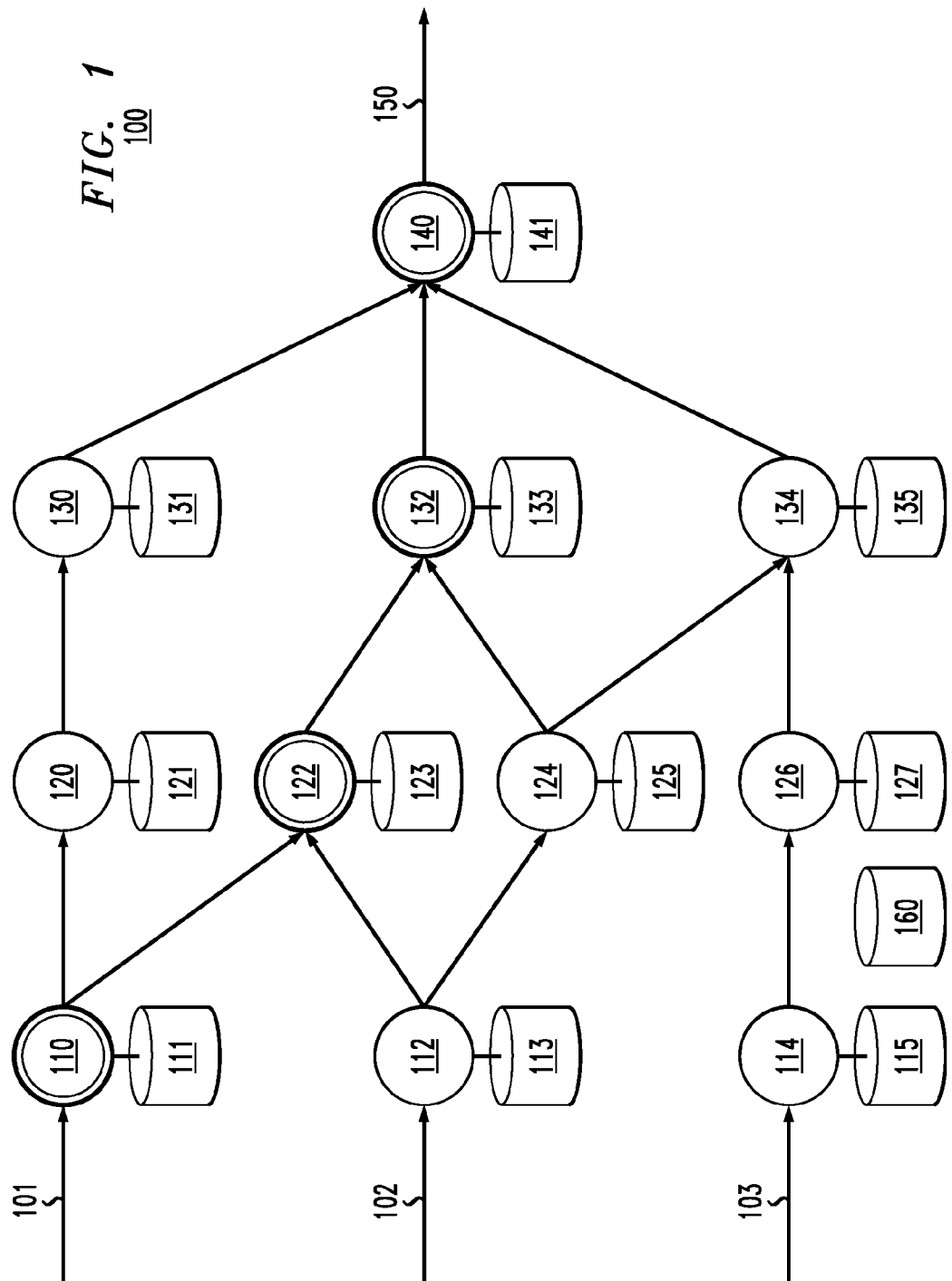
FIG. 1 illustrates a data stream processing system, represented by a graph, in which one or more embodiments of the invention can be implemented.

Embodiments of the present invention will be explained below in the context of an illustrative data stream processing system. However, it is to be understood that the present invention is not limited to any particular data processing system. Rather, the invention is more generally applicable to any data processing system in which it would be desirable to maintain provenance data. As illustratively used herein, the term "provenance" is defined as "origin" or "source." Thus, for example, provenance data (or provenance information) is data that records information pertaining to how other data is causatively derived.

One illustrative real-world, practical application of principles of the invention is the domain of healthcare. Specifically, in the healthcare domain, one might envision a stream processing infrastructure that takes, as input, streams of medical information such as streams of electroencephalogram (EEG) or electrocardiogram (ECG) data as well as blood pressure, weight, glucometer readings and the like. The stream processing infrastructure would apply analytic algorithms to these data streams and identify significant medical events that warrant further attention from a doctor or other medical professional. In such a system, it is important to give the medical professional as much information about the generation of the significant medical event as possible, including meta-information, referred to herein as provenance data, such as what subsets of the input and intermediate data streams triggered the significant medical event and what specific processing elements contributed to its generation. The medical professional who receives the alert generated by the stream processing system may issue a provenance query related to the alert, where the provenance query is a request to show or reveal the stream data items and the stream processing nodes that contributed to the generation of the alert. Again, it is to be appreciated that while the solution domain mentioned in this embodiment is healthcare, principles of the invention apply to any domain where stream processing can be applied.

Thus, principles of the invention address: (a) how to proactively determine, for only an appropriate subset of analysis results, precisely what sequence of processing elements participated in the generation of an analysis result and what stream data samples contributed to the generation of the analysis result; and (b) how to store this proactively determined set of causative processing elements and stream data samples for a duration that reflects the likely or expected query patterns desiring this causative information.

In one embodiment of the present invention, a system maintains meta-information about the processing of each stream segment. The streaming framework is designed to process the streaming data quickly and efficiently. In the event that an alert is raised and the recipient of that alert wants to understand its origins, the system is capable of determining those origins. In order to do so, however, the system processes the extensive records maintained by the stream processing framework in order to find the entries that correspond to this alert. We refer to this solution as "provenance backtracing."

FIG. 1 illustrates a stream processing system represented by graph 100. This graph has eleven processing elements: 110, 112, 114, 120, 122, 124, 126, 130, 132, 134, and 140. The processing elements are connected via communication paths represented by the directional arrows connecting them. The processing elements each have a database in which to store information, as represented by 111, 113, 115, 121, 123, 125, 127, 131, 133, 135, and 141. The processing elements can manipulate the data in arbitrary ways. For example, a simple processing element could identify for further processing only those data elements exceeding a particular threshold. Alternatively, a processing element may take as input several data streams and generate as output a data stream whose values represent averages of the corresponding samples of input data. A more complex processing element might detect anomalies by analyzing the morphology of the incoming stream or look for complex patterns in the incoming data using pattern recognition algorithms (e.g., neural network, support vector machine).

Data streams, 101, 102, and 103 enter the stream processing system at processing elements 110, 112, and 114, respectively. As each processing element processes the stream according to its individual algorithm, which could perform any computation on the stream of data as discussed above, the processing element passes the resultant output to the next processing element according to the connections in graph 100. In our examples from above, the processing element looking for data elements exceeding a particular threshold would only output those outputs exceeding that threshold and the processing element looking for complex patterns would only output data exhibiting those patterns. When the last processing element, processing element 140 in this graph, finishes it's processing, any outputs 150 are sent for notification or alert as specified by the stream processing applications deployed on the stream processing system.

When an alert is received by a medical professional, this professional might want to understand the data that was used in generating that event. For example, what sensors produced the original data used in generating the event or what processing elements participated in generating the event? Or, alternatively, what was the original set of data elements that led to the generation of the alert? As an example, a medical professional may receive a 'congestive heart failure' alert generated by a processing graph operating on a combination of ECG, blood pressure (BP) and weight sensor streams and wish to query the set of relevant ECG, BP and weight values that caused the generation of this alert.

Figure 2:
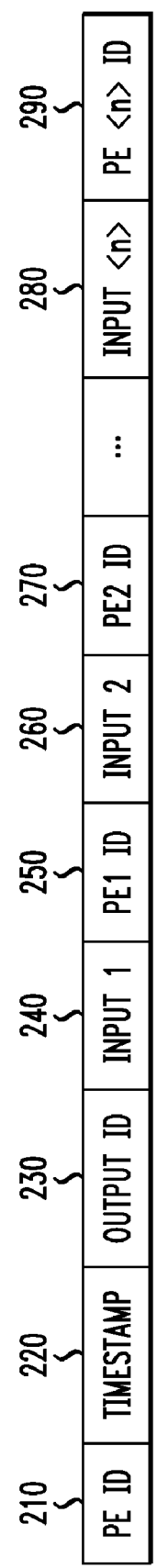
FIG. 2 illustrates meta-information recorded by a processing element, according to an embodiment of the invention.

In order to answer such a provenance query (a request to obtain provenance information about an output value), provenance information is generated during processing in the processing elements. One way to do this is to have each processing node record the relationship between each output it generates and the inputs that contributed to that output. This meta-information recorded by the processing element is illustrated by database element 200 in FIG. 2. When an output event is generated, a data structure in the form of a record is stored in the database associated with the processing element that generated the event. This record 200 contains the identity of the processing element 210, the time at which the event was generated (timestamp) 220, the unique identifier representing this output event 230, as well as a record of all the input elements 240, 260, and 280 (and the processing elements that generated them 250, 270, 290) that contributed to this output event 230. This record is stored in the database associated with the processing element identified in 210.

Referring back to FIG. 1, if processing element 132 generated an event 230, then the database 133 would maintain a record of event 230. This database record would contain all the information contributing to this event and would include processing element 132 as the PE ID 210 in the database record. Note that the database containing the IDs of all the stream samples and the associated meta-information can be either stored on a centralized server or distributed across a set of servers.

When a provenance query about a given alert event occurs, the meta-information stored by the processing element that generated the alert is consulted to identify all inputs associated with the alert. Once these input events have been identified, the meta-information stored by the upstream analysis components which generated the input events are used to determine further upstream events that are indirectly related to the alert. This process is repeated recursively until all events related to the alert have been identified and the original data sources have been identified together with all processing elements involved in processing these data elements. It is worth noting that the term "alert" here refers to a generic subset of the output events generated by any given processing graph.

As mentioned before, consumers of these processed events may or may not issue the provenance query on any specific output sample. In many cases, all of the outputs generated by a stream processing system may be considered to be alerts, as any of those outputs could be viewed as the basis on which the consumer of these outputs issues a provenance query.

In the provenance query backtracing described above, each node places its relevant meta-information in a provenance query results store (160 in FIG. 1). At the end of the backtracing process, this store has all of the information needed to answer the provenance query. Even though not explicitly shown in FIG. 1 for clarity purposes, each processing node (110, 112, 114, 120, 122, 124, 126, 130, 132, 134, and 140) has a link to store into and retrieve from the provenance query results store (160).

Unfortunately, provenance function backtracing is a tedious and time-consuming process. Due to the high data volumes typically associated with electronic stream processing systems, we can expect that much of the information in the database 133 above would be archived or pushed to secondary storage after a relatively short period of time. In many scenarios, the query for the provenance will typically occur fairly soon after the generation of the "alert." But even this may be after the relevant portions of the data stream have been archived; in many other instances, the queries may occur significantly later, e.g., 6 or 10 years after the generation of the alert. Moreover, even if the information were stored in primary storage, performing the backtracing process itself may involve the retrieval of a large number of stream samples and processing elements—this may itself consume an appreciable amount of time. Although this approach of query-driven backtracing is the minimally acceptable solution to the problem, it may not be sufficient when the queries are dealing with time-critical medical information about a patient whose life could depend upon the answers. That is, widespread adoption of automated analytics for streaming data depends on the ability to assure quick and rapid responses to queries on the provenance of the output generated by those analytics.

Consequently, in accordance with principles of the invention, the system performs provenance function backtracing at the time alerts occur rather than waiting for a corresponding provenance query. When alerts occur, provenance function backtracing is performed immediately—without waiting for a provenance query to arrive. By triggering the calculation of provenance information at the time of the alert, the system can be ready for subsequent provenance queries when they are submitted. Proactive calculation of this provenance information is most efficient when it is performed on a relatively small subset of the output data samples—in other words, alerts that are likely to result in provenance queries should be relatively rare. Moreover, the process of proactive provenance calculation has to be aware of the specific set of outputs which are designated as alerts, and the typical or expected query pattern that is associated with such alerts.

Referring back to FIG. 1, suppose that output 150 is produced as a result of the computations performed at processing elements 110, 122, 132, and 140. We illustrate this in FIG. 1 by showing these processing elements with double outlines. Unfortunately, in the existing art, there is no way to know that this is why and how this output was generated. Principles of the invention relate to how to record this meta-information about the computation in an efficient way. We propose to use an overlay framework with the same topology as the original analysis framework. Each element in our overlay has access to the records of its original analysis counterpart. Processing in the overlay framework occurs in the reverse direction as compared to the original. Our overlay framework is illustrated in FIG. 3.

Figure 3:
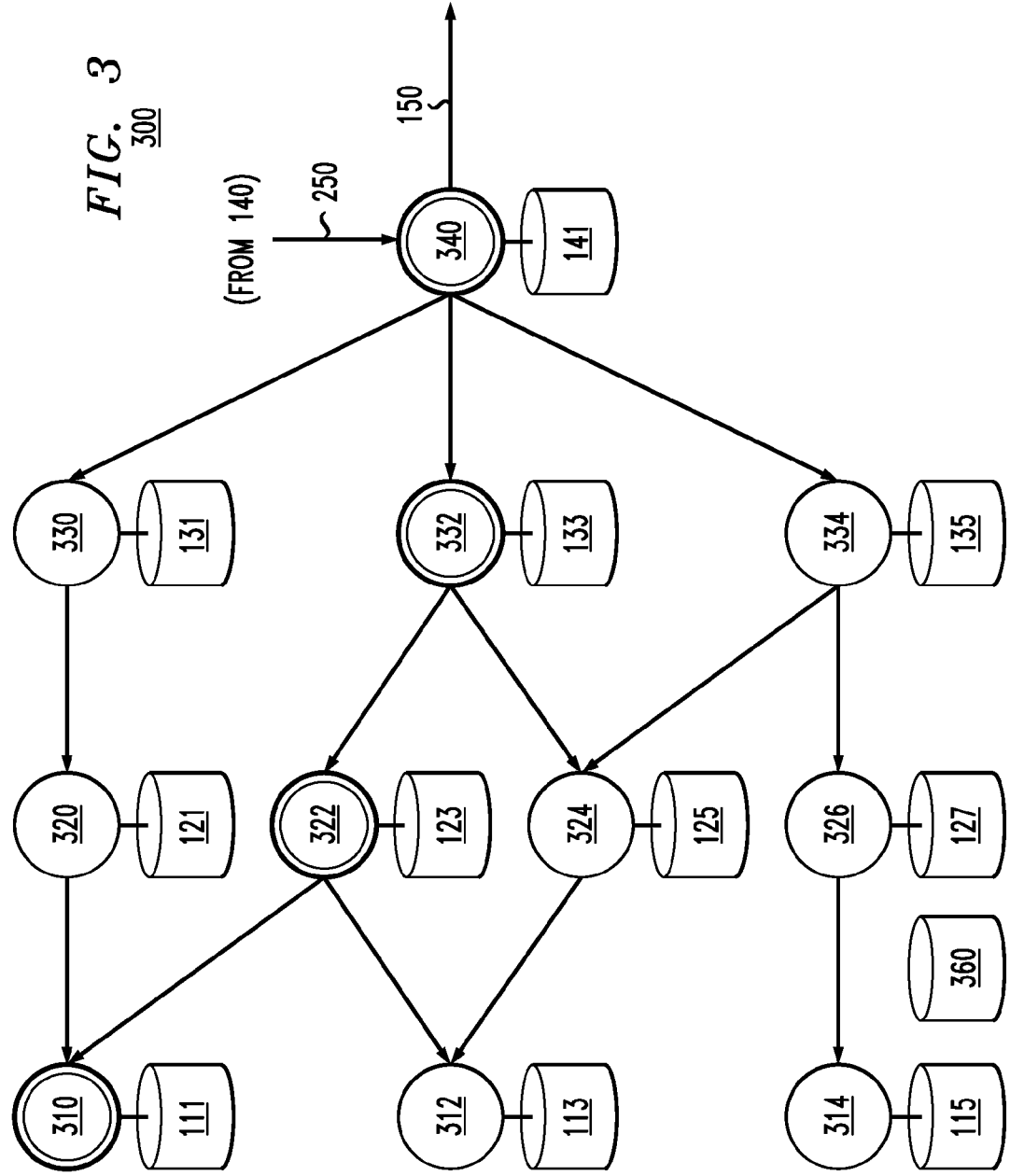
FIG. 3 illustrates a provenance overlay, represented by a graph, according to an embodiment of the invention.

FIG. 3 illustrates a provenance overlay represented by graph 300. This provenance overlay graph corresponds to the stream processing graph 100 of FIG. 1. Like graph 100, our provenance overlay has eleven process elements: 310, 312, 314, 320, 322, 324, 326, 330, 332, 334, and 340. These processing elements correspond on a one-to-one basis with the processing elements of FIG. 1. So, for example, processing element 310 of FIG. 3 corresponds to processing element 110 of FIG. 1. The processing elements are connected via communication paths represented by the directional arrows connecting them. Notice that the communication paths in our provenance overlay graph 300 occur in the reverse direction as compared to the stream processing graph 100. The processing elements in both the stream processing graph 100 and the provenance overlay 300 share a database, as represented by 111, 113, 115, 121, 123, 125, 127, 131, 133, 135, and 141. The processing elements of the stream processing graph 100 write data into this database and the processing elements of the provenance overlay graph 300 read data out of this database. The storage element 360 is the same as the provenance query results store 160 in FIG. 1.

Recall that output alert 150 was generated by processing element 140 of the stream processing graph. Recall also that processing elements 132, 122, and 110 each contributed to the generation of this event. Recall also that data element 101 was assumed to be the sole piece of data that lead to this output alert. Recall that when the last processing element, processing element 140 in this graph, finishes its processing, any outputs 150 are sent for notification or alert as specified by the stream processing system. In our improved implementation, when processing element 140 completes its processing and alert notification process as previously specified in the stream processing graph 100, it now also alerts the provenance overlay processing element 340.

Figure 4:
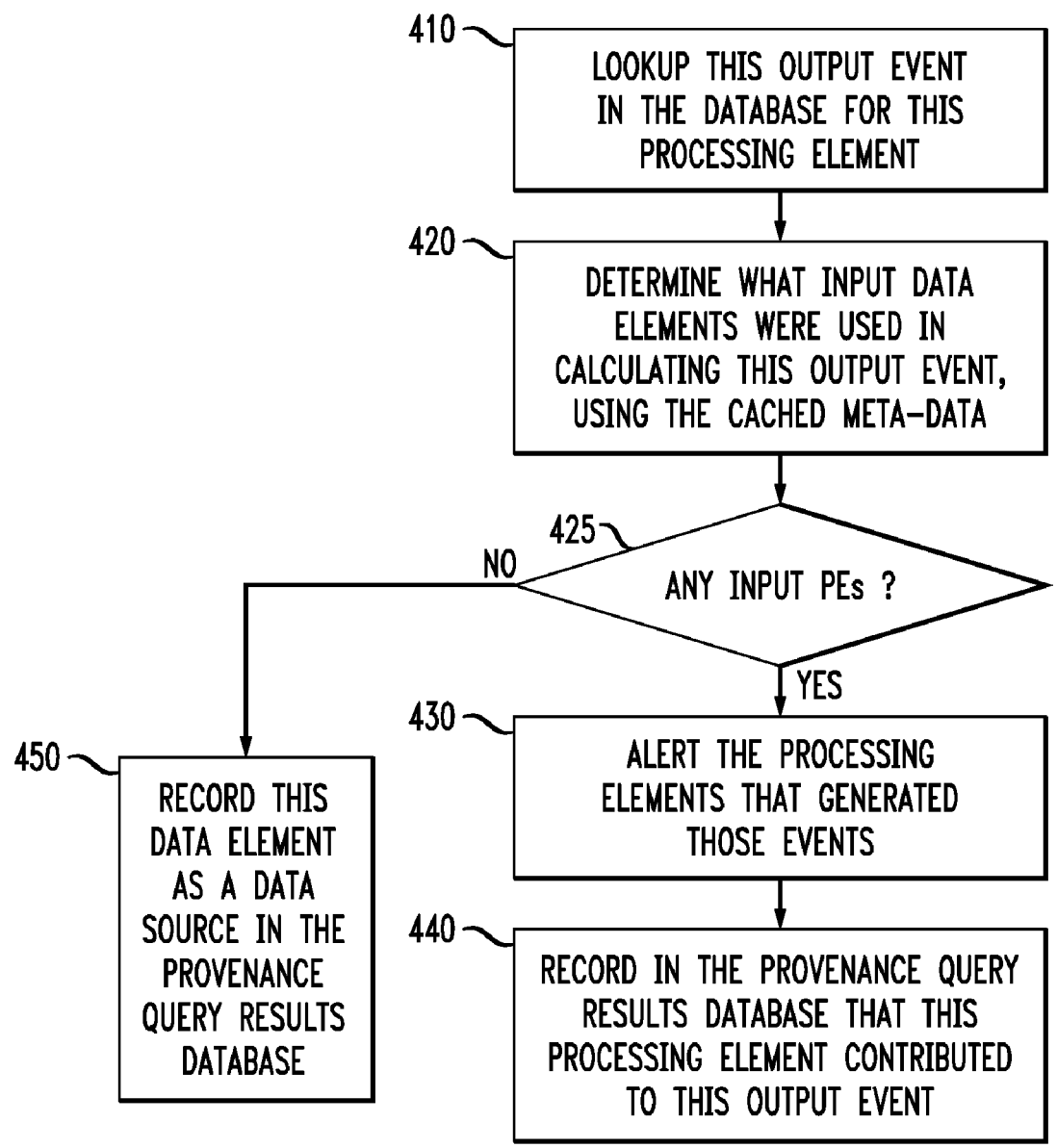
FIG. 4 illustrates a method for performing provenance data maintenance, according to an embodiment of the invention.

Upon receiving notification that an output alert was generated, processing element 340 performs algorithm 400, illustrated in FIG. 4, as long as the output alert corresponds to one for which the system has determined that a proactive computation of the provenance is appropriate. Processing element 340 begins by looking up (410) this given output ID in database 141. From this database record, processing element 340 determines (420) what, if any, input elements were used by processing element 140 in generating this output alert. It also identifies (425) which processing elements generated those input elements. With this information, processing element 340 alerts (430) those processing elements that generated data used as input in this calculation of their role in generating the alert. Processing element 340 then records (440) that it contributed to specified output alert. Alternatively, if no processing elements generated the input (425), then the input is considered to be source data and the processing element records (450) this data element as being source data in the provenance query results database.

In our example, processing element 340 alerts processing element 332, because it is associated with the only processing element (132) involved in generating the input associated with this output alert, of the input identifiers that contributed to this output alert. Processing element 332 continues this processing by performing algorithm 400 using the data it received from processing element 340. Processing element 332 will ultimately notify processing element 322. Processing element 322 performs algorithm 400 and will ultimately notify processing element 310. Processing element 310 identifies data element 101 as being the data source for output alert 150.

Upon completion of algorithm 400, the provenance query results database contains a record of all processing elements and source data elements that contributed to the generation of each output alert. When a provenance query arrives, the stream processing framework need only consult this one database to respond to the query.

The storage elements 111, 113, 115, 121, 123, 125, 127, 131, 133, 135, and 141 are caches. After the cache is full, each placement into the cache is accompanied by a removal from the cache. Elements removed from the cache can be maintained in a nonvolatile data store where they can be made available for future accesses. It can be generally assumed that the cache provides much lower access latency and higher performance than the nonvolatile data store.

Figure 5:
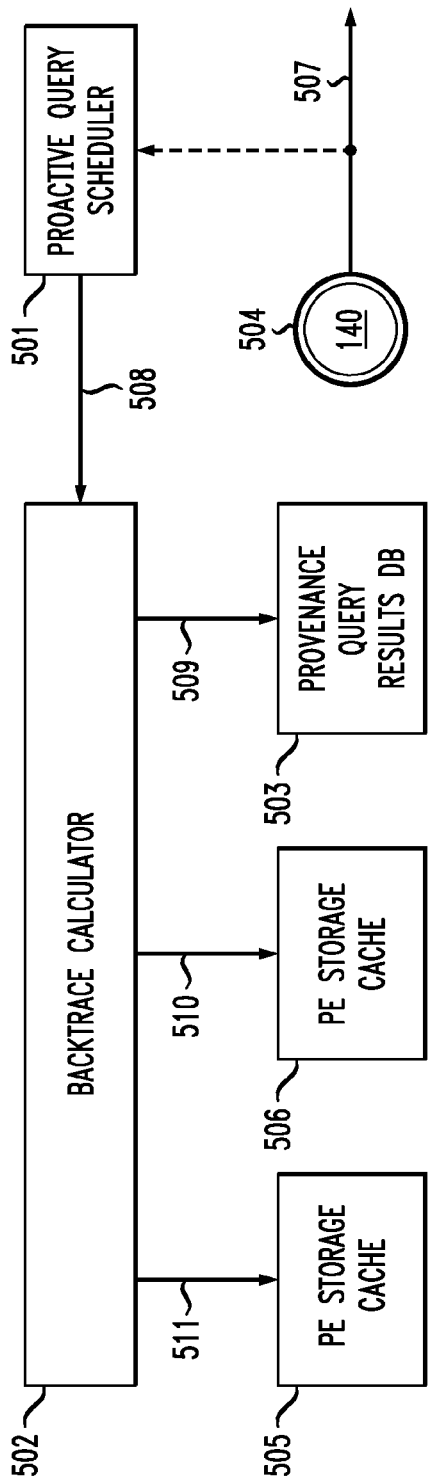
FIG. 5 illustrates an architectural overview of components employed to support provenance data maintenance, according to an embodiment of the invention.

The embodiment described above dictates that the algorithm 400 be invoked selectively, only for the set of alerts for which proactive computation of provenance is deemed appropriate. FIG. 5 shows an architectural overview of the components required to support this embodiment of the invention. The process of computing and storing the provenance result is initially triggered when the output PE 504 of a processing graph generates an output sample or "alert." The Proactive Query Scheduler component 501 is made aware of this generated alert and is then responsible for internally deciding if and when a proactive computation of the provenance results is warranted. The mechanism for deciding this may include one or more of a variety of techniques, such as: (a) explicit rule-based triggering, whereby a rule indicates that a specific type of alert warrants a precomputation and storage of the provenance results; and (b) learning-based triggering, where the past history of actually issued provenance queries is used to compute, via automatic learning algorithms, the likelihood of a particular alert being associated with one or more queries within a specific future duration. Principles of the invention are not limited to the specific mechanism used for determining the trigger for a precomputation, thus a variety of well known state-of-the-art techniques may be used for this purpose.

When the Proactive Query Scheduler has determined that a proactive provenance result computation is warranted, it informs (508) the Backtrace calculator component 502, which in turn will invoke the algorithm 400 described previously in FIG. 4. It is to be noted that the execution of the algorithm 400 will effectuate invocation of and retrieval of data from the caches 505, 506 where the metadata of the intermediate steps of the stream processing graph are stored. As a result of this computation, the generated provenance results are stored (509) in the Provenance Query Result Database 503, where it is readily available in case a query actually occurs.

In yet another embodiment of the invention, the system only performs provenance function backtrace caching at the time the alert occurs, but does not calculate the provenance query results until the time of the query. This technique balances the need for timely responses with the need to avoid unnecessary computation. In this embodiment, the data contributing to an output alert are marked as having high provenance value, ensuring that the data is retained in the cache for a longer time than data not so marked. In terms of FIG. 5, this corresponds to instructions 511, 510 from the Backtrace calculator component to the PE caches 505, 506 respectively, marking specific data in those caches that would be needed to reconstruct the provenance query or queries most likely to be issued due to the generation of the alert 507.

Marking the data may have multiple purposes. One form of marking is merely to differentially prioritize the data in the cache, thereby ensuring that the data needed for reconstructing the answers to the more likely provenance queries are retained in the cache preferentially over the data that are less likely to be required. Another form of marking might be to indicate a specific length of time for which the data in the cache should be retained or the specific function by which the priority level of the cached data element should be diminished or decayed over time. For example, the data could be marked as expiring in 24 hours, in 7 days or as having its priority level drop by one level with every passing hour. Alternatively, it could be marked of interest to N potential queries. As each potential query is post-processed, the count would be decremented. Upon the final decrement, the priority of the data could be lowered and the data could be moved to tertiary storage together with data that was not involved in generating an alert. This technique supports provenance queries for all kinds of data (even data not associated with an alert) but it optimizes the query response time for data associated with an alert.

Because alerts are expected to be relatively infrequent compared to the total amount of data coming into the system and because provenance queries are only expected to occur as a result of alerts, post-processing in this way offers the advantage of maintaining the high efficiency for the common case while simultaneously improving the efficiency over the provenance function backtracing solution. Note also that each of the marking techniques described here for the data in the PE caches can be applied to the reconstructed provenance data stored in the Provenance Query Results DB as well—for example, if prior usage history indicates that a particular alert generates no more than two provenance queries, then the precomputed provenance result can be removed from the Provenance Query Results DB after it has been retrieved in response to two separate provenance queries.

It is to be noted that the Proactive Query Scheduler 501 essentially uses the output alert 507 to generate a schedule for invoking the backtrace calculator. In the description of the steps above, the scheduling step was immediate—the request 508 to precompute the provenance information was generated immediately in response to the generation of an alert. While this is likely to be a common situation (as many provenance queries are likely to occur soon after an alert is delivered to a consumer), principles of the invention permit a variety of other schedules for triggering the precomputation. For example, if the Proactive Query Scheduler knows that "arrhythmia" alerts are typically studied by a cardiac specialist who visits the clinic and studies weekly alerts every Monday morning, then the Proactive Query Scheduler may choose to trigger the provenance precomputation only on Sunday evening, rather than immediately after every arrhythmia alert. In this case, the Proactive Query Scheduler may also choose to mark the data, in the cache of each processing element involved in the generation of the arrhythmia alert, to ensure that it is cached until Monday morning.

In the descriptions above, the backtrace processing was performed in each of the processing nodes. However, if the provenance caches (111, 113, 115, 121, 123, 125, 127, 131, 133, 135, 141) are accessible by a single processing entity, that processing entity can perform the backtrace processing. Principles of the invention are not limited to the illustrative forms of backtrace processing described above.

One known solution is to manage the data in the cache via a Least Recently Used (LRU) policy. Unfortunately, LRU-based management does not necessarily reflect the value of the data itself. Another known solution is to mark all data that occurred within the last T seconds (or other unit of time), but this will cause the system to maintain a much larger amount of data than our technique. These techniques do not differentiate between "routine data" (data that did not result in an alert) and "suspicious data" (data that did result in an alert). The inventive solution does and offers the ability of much more efficient data management.

Figure 6:
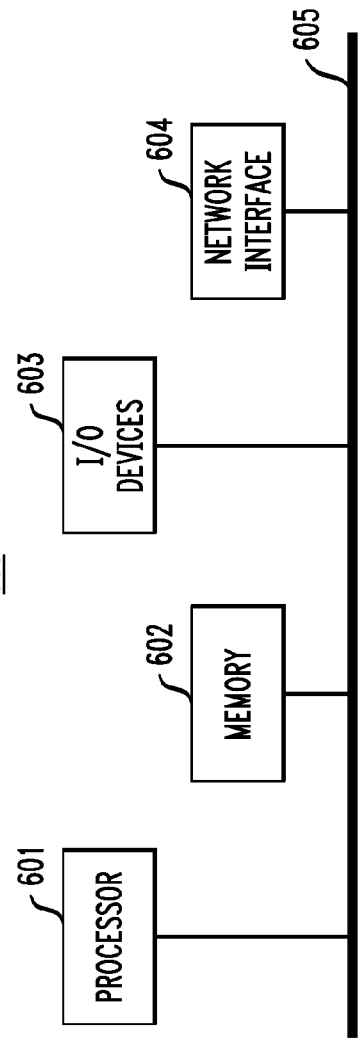
FIG. 6 illustrates a computer system in accordance with which one or more components/steps of the techniques of the invention may be implemented.

Lastly, FIG. 6 illustrates a computer system 600 in accordance with which one or more components/steps of the techniques of the invention may be implemented. It is to be further understood that the individual components/steps may be implemented on one such computer system or on more than one such computer system. In the case of an implementation on a distributed computing system, the individual computer systems and/or devices may be connected via a suitable network, e.g., the Internet or World Wide Web. However, the system may be realized via private or local networks. In any case, the invention is not limited to any particular network.

Thus, the computer system shown in FIG. 6 may represent one or more servers or one or more other processing devices capable of providing all or portions of the functions described herein. Alternatively, FIG. 6 may represent a mainframe computer system.

The computer system may generally include a processor 601, memory 602, input/output (I/O) devices 603, and network interface 604, coupled via a computer bus 605 or alternate connection arrangement.

It is to be appreciated that the term "processor" as used herein is intended to include any processing device, such as, for example, one that includes a CPU and/or other processing circuitry. It is also to be understood that the term "processor" may refer to more than one processing device and that various elements associated with a processing device may be shared by other processing devices.

The term "memory" as used herein is intended to include memory associated with a processor or CPU, such as, for example, RAM, ROM, a fixed memory device (e.g., hard disk drive), a removable memory device (e.g., diskette), flash memory, etc. The memory may be considered a computer readable storage medium.

In addition, the phrase "input/output devices" or "I/O devices" as used herein is intended to include, for example, one or more input devices (e.g., keyboard, mouse, etc.) for entering data to the processing unit, and/or one or more output devices (e.g., display, etc.) for presenting results associated with the processing unit.

Still further, the phrase "network interface" as used herein is intended to include, for example, one or more transceivers to permit the computer system to communicate with another computer system via an appropriate communications protocol.

Accordingly, software components including instructions or code for performing the methodologies described herein may be stored in one or more of the associated memory devices (e.g., ROM, fixed or removable memory) and, when ready to be utilized, loaded in part or in whole (e.g., into RAM) and executed by a CPU.

In any case, it is to be appreciated that the techniques of the invention, described herein and shown in the appended figures, may be implemented in various forms of hardware, software, or combinations thereof, e.g., one or more operatively programmed general purpose digital computers with associated memory, implementation-specific integrated circuit(s), functional circuitry, etc. Given the techniques of the invention provided herein, one of ordinary skill in the art will be able to contemplate other implementations of the techniques of the invention.

Although illustrative embodiments of the present invention have been described herein with reference to the accompanying drawings, it is to be understood that the invention is not limited to those precise embodiments, and that various other changes and modifications may be made by one skilled in the art without departing from the scope or spirit of the invention.

What is claimed is:

1. A method for processing data associated with a data stream received by a data stream processing system, wherein the system comprises a plurality of processing elements, the method comprising the steps of:

maintaining a portion of data associated with the data stream, wherein the maintained data comprises inputs to each processing element that contributed to an output of each processing element;

in response to an alert generated by one of the processing elements, triggering a scheduler to determine when a pre-calculation of a prospective query related to the alert should be executed; and when the scheduler determines that a pre-calculation of a prospective query related to the alert should be executed, using at least a portion of the maintained data to determine a set of data that contributed to the alert such that the alert-contributing set of data can be used to respond to the prospective query upon arrival thereof, wherein determination of the alert-contributing set of data comprises:

representing the data stream processing system as a processing graph wherein nodes of the processing graph correspond to processing elements in the data stream processing system and links in the processing graph correspond to communication paths between the processing elements;

creating an overlay graph wherein nodes in the overlay graph correspond to nodes in the processing graph, and links in the overlay graph correspond to links in the processing graph wherein each link in the overlay graph is a reverse of the corresponding link in the processing graph, and the overlay nodes operate concurrently with the nodes in the processing graph, wherein the overlay graph and the corresponding processing graph are separate entities;

starting with a node that generated the alert, each node uses dependency information to forward to its linked nodes data that was forwarded to its corresponding node in the processing graph from the processing graph node corresponding to the linked node and that contributed to the alert; and continuing with backtrack processing to the overlay nodes that correspond to an input node of the processing graph until all data stream data and all functions executing on the processing node graph that contributed to the alert have been specified.

2. The method of claim 1, further comprising the step of storing the alert-contributing set of data in a query results storage element.

3. The method of claim 1, wherein an alert comprises a computation result of interest.

4. The method of claim 1, wherein the alert-contributing set of data is stored for a designated duration.

5. The method of claim 1, wherein the alert-contributing set of data is marked for storage with a retention value that is based on a priority associated with the alert.

6. The method of claim 1, wherein the step of triggering the scheduler further comprises associating the alert with one or more classes of alerts.

7. The method of claim 6, wherein the scheduler generates a schedule based on a history of prior queries issued for a corresponding class of alerts.

8. The method of claim 7, wherein the scheduler generates a schedule based on a rule describing likely time instants at which a query for the corresponding class of alerts may be issued.

9. Apparatus for processing data associated with a data stream received by a data stream processing system, wherein the system comprises a plurality of processing elements, the apparatus comprising:

a memory; and
    a processor coupled to the memory and configured to:
    maintain a portion of data associated with the data stream, wherein the maintained data comprises inputs to each processing element that contributed to an output of each processing element;

in response to an alert generated by one of the processing elements, trigger a scheduler to determine when a pre-calculation of a prospective query related to the alert should be executed; and when the scheduler determines that a pre-calculation of a prospective query related to the alert should be executed, use at least a portion of the maintained data to determine a set of data that contributed to the alert such that the alert-contributing set of data can be used to respond to the prospective query upon arrival thereof, wherein determination of the alert-contributing set of data comprises:

representing the data stream processing system as a processing graph wherein nodes of the processing graph correspond to processing elements in the data stream processing system and links in the processing graph correspond to communication paths between the processing elements;

creating an overlay graph wherein nodes in the overlay graph correspond to nodes in the processing graph, and links in the overlay graph correspond to links in the processing graph wherein each link in the overlay graph is a reverse of the corresponding link in the processing graph, and the overlay nodes operate concurrently with the nodes in the processing graph, wherein the overlay graph and the corresponding processing graph are separate entities;

starting with a node that generated the alert, each node uses dependency information to forward to its linked nodes data that was forwarded to its corresponding node in the processing graph from the processing graph node corresponding to the linked node and that contributed to the alert; and continuing with backtrack processing to the overlay nodes that correspond to an input node of the processing graph until all data stream data and all functions executing on the processing node graph that contributed to the alert have been specified.

10. The apparatus of claim 9, wherein the processor is further configured to store the alert-contributing set of data in a query results storage element.

11. The apparatus of claim 9, wherein an alert comprises a computation result of interest.

12. The apparatus of claim 9, wherein the alert-contributing set of data is stored for a designated duration.

13. The apparatus of claim 9, wherein the alert-contributing set of data is marked for storage with a retention value that is based on a priority associated with the alert.

14. The apparatus of claim 9, wherein triggering the scheduler further comprises associating the alert with one or more classes of alerts.

15. The apparatus of claim 14, wherein the scheduler generates a schedule based on at least one of: a history of prior queries issued for a corresponding class; and a rule describing likely time instants at which a query for the corresponding class of alerts may be issued.

16. An article of manufacture for processing data associated with a data stream received by a data stream processing system, wherein the system comprises a plurality of processing elements, the article comprising a computer readable storage medium having one or more programs embodied therewith wherein the one or more programs, when executed by a computer, perform steps of:

maintaining a portion of data associated with the data stream, wherein the maintained data comprises inputs to each processing element that contributed to an output of each processing element;

in response to an alert generated by one of the processing elements, triggering a scheduler to determine when a pre-calculation of a prospective query related to the alert should be executed; and when the scheduler determines that a pre-calculation of a prospective query related to the alert should be executed, using at least a portion of the maintained data to determine a set of data that contributed to the alert such that the alert-contributing set of data can be used to respond to the prospective query upon arrival thereof, wherein determination of the alert-contributing set of data comprises:

representing the data stream processing system as a processing graph wherein nodes of the processing graph correspond to processing elements in the data stream processing system and links in the processing graph correspond to communication paths between the processing elements;

creating an overlay graph wherein nodes in the overlay graph correspond to nodes in the processing graph, and links in the overlay graph correspond to links in the processing graph wherein each link in the overlay graph is a reverse of the corresponding link in the processing graph, and the overlay nodes operate concurrently with the nodes in the processing graph, wherein the overlay graph and the corresponding processing graph are separate entities;

starting with a node that generated the alert, each node uses dependency information to forward to its linked nodes data that was forwarded to its corresponding node in the processing graph from the processing graph node corresponding to the linked node and that contributed to the alert; and continuing with backtrack processing to the overlay nodes that correspond to an input node of the processing graph until all data stream data and all functions executing on the processing node graph that contributed to the alert have been specified.

* * * * *